(12) United States Patent
Gibson et al.

(10) Patent No.: US 11,872,374 B2
(45) Date of Patent: Jan. 16, 2024

(54) DRUG DELIVERY DEVICE HAVING A NEEDLE GUARD MECHANISM WITH A TUNABLE THRESHOLD OF RESISTANCE TO NEEDLE GUARD MOVEMENT

(71) Applicant: AMGEN INC., Thousand Oaks, CA (US)

(72) Inventors: Scott R. Gibson, Granada Hills, CA (US); Sheldon Moberg, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/951,987

(22) Filed: Nov. 18, 2020

(65) Prior Publication Data
US 2021/0069416 A1 Mar. 11, 2021

Related U.S. Application Data

(63) Continuation of application No. 15/540,114, filed as application No. PCT/US2016/019870 on Feb. 26, 2016.

(Continued)

(51) Int. Cl.
*A61M 5/20* (2006.01)
*A61M 5/24* (2006.01)
*A61M 5/32* (2006.01)

(52) U.S. Cl.
CPC ............. *A61M 5/20* (2013.01); *A61M 5/24* (2013.01); *A61M 5/3243* (2013.01); *A61M 5/3202* (2013.01); *A61M 2005/2013* (2013.01)

(58) Field of Classification Search
CPC ........ A61M 5/20; A61M 5/24; A61M 5/3243; A61M 5/3202; A61M 2005/2013;
(Continued)

(56) References Cited

U.S. PATENT DOCUMENTS 4,752,290 A 6/1988 Schramm
6,099,503 A * 8/2000 Stradella ............. A61M 5/2033
604/131

(Continued)

FOREIGN PATENT DOCUMENTS

EP 2090326 A1 8/2009
EP 2662104 A1 11/2013
(Continued)

OTHER PUBLICATIONS

International Search Report for International Application No. PCT/US2016/019870, dated Jun. 8, 2016.
(Continued)

*Primary Examiner* — Emily L Schmidt
*Assistant Examiner* — Alexandra Lalonde
(74) *Attorney, Agent, or Firm* — MARSHALL, GERSTEIN & BORUN LLP

(57) ABSTRACT

A device and method for drug delivery includes a casing for housing a drug storage container, the container including a dose delivery member, at least a portion of the dose delivery member extending through an opening in the casing; a guard movable relative to the casing between extended and retracted positions; an interference arrangement for providing selected threshold of resistance to movement of the guard from the extended position to the retracted position during insertion of the dose delivery member into body tissue at an injection site, the arrangement having a first member and a second member, the first and second members engaging one another to retain the guard in the extended position, one of the first and second members moving if the selected threshold of resistance is exceeded to allow the members to slide past one another to allow the guard to move into the retracted position.

23 Claims, 11 Drawing Sheets

Related U.S. Application Data

(60) Provisional application No. 62/121,758, filed on Feb. 27, 2015.

(58) Field of Classification Search
CPC .. A61M 5/2033; A61M 5/3257; A61M 5/326; A61M 2005/2073; A61M 2005/3247; A61M 2005/3267; A61M 2005/3268; A61M 2005/3254; A61M 2005/208; A61M 2005/3261; A61M 2005/3263; A61M 5/00; A61M 5/178; A61M 5/31565; A61M 5/31566; A61M 5/31571; A61M 5/3158; A61M 5/31585; A61M 5/3221; A61M 5/3232; A61M 5/3234; A61M 5/3245; A61M 5/2066; A61M 2005/202; A61M 2005/2026; A61M 2005/3227; A61M 2005/3252; A61M 2005/3264; A61M 5/3205; A61M 5/3213; A61M 5/3271; A61M 5/3269; A61M 5/3273; A61M 5/3275; A61M 2005/3215; A61M 2005/3246; A61M 2005/325; A61M 2005/3256; A61M 2005/3258; A61M 2005/3265

See application file for complete search history.

(56) References Cited

U.S. PATENT DOCUMENTS

| | | | |
|---|---|---|---|
| 6,533,819 | B1 | 3/2003 | Urry et al. |
| 6,689,107 | B1 | 2/2004 | Choudhary |
| 6,796,967 | B2 | 9/2004 | Jensen |
| 2003/0078546 | A1 | 4/2003 | Jensen |
| 2007/0265568 | A1* | 11/2007 | Tsals ................. A61M 5/2033 604/890.1 |
| 2010/0191217 | A1* | 7/2010 | Hommann .......... A61M 5/2033 604/506 |
| 2010/0256570 | A1* | 10/2010 | Maritan .............. A61M 5/2033 604/198 |
| 2011/0077592 | A1 | 3/2011 | Takemoto |
| 2011/0196339 | A1 | 8/2011 | Hirschel et al. |
| 2012/0116319 | A1* | 5/2012 | Grunhut ................. A61M 5/20 604/198 |
| 2012/0226233 | A1 | 9/2012 | Schraga |
| 2013/0281939 | A1 | 10/2013 | Roberts et al. |
| 2013/0310759 | A1* | 11/2013 | Hourmand ........... A61M 5/326 604/198 |
| 2014/0207073 | A1 | 7/2014 | Shang et al. |
| 2015/0246181 | A1 | 9/2015 | Fourt et al. |
| 2016/0106920 | A1 | 4/2016 | Stefansen |

FOREIGN PATENT DOCUMENTS

| | | |
|---|---|---|
| FR | 2905273 A1 | 3/2008 |
| JP | 2013-534164 A | 9/2013 |
| WO | WO-02/09797 A1 | 2/2002 |
| WO | WO-2012/022810 A2 | 2/2012 |
| WO | WO-2012045833 A1 | 4/2012 |
| WO | WO-2012093071 A1 | 7/2012 |

OTHER PUBLICATIONS

Written Opinion of the International Searching Authority, International Application No. PCT/US2016/019870, dated Jun. 8, 2016.
European Patent Application No. 16 708 912.7, Communication Pursuant to Article 94(3) EPC, dated Jan. 7, 2020.
Japanese Patent Application No. 2017-542827, Notice of Rejection, dated Jan. 7, 2020.
European Patent Application No. 16708912.7, Summons to Attend Oral Proceedings Pursuant to Rule 115(1) EPC, dated Feb. 10, 2021.
U.S. Appl. No. 15/540,114, Nonfinal Office Action, dated Dec. 22, 2021.
U.S. Appl. No. 15/540,114, Nonfinal Office Action, dated Jun. 22, 2022.
U.S. Appl. No. 15/540,114, Final Office Action, dated Jan. 4, 2023.
Japanese Patent Application No. 2022-039981, Notice of Rejection, dated Feb. 21, 2023.

\* cited by examiner

DRUG DELIVERY DEVICE HAVING A NEEDLE GUARD MECHANISM WITH A TUNABLE THRESHOLD OF RESISTANCE TO NEEDLE GUARD MOVEMENT

CROSS-REFERENCE TO RELATED APPLICATIONS

This is a continuation of U.S. patent application Ser. No. 15/540,114, filed Jun. 27, 2017, which is U.S. National Stage of International Patent Application No. PCT/US2016/019870, filed Feb. 26, 2016, which claims priority to U.S. Provisional Application No. 62/121,758, filed Feb. 27, 2015. The entire contents of International Patent Application No. PCT/US2016/019870 and U.S. Provisional Application No. 62/121,758 are expressly incorporated herein by reference for all purposes.

FIELD OF THE DISCLOSURE

The present disclosure relates to drug delivery devices. More particularly, the present disclosure relates to drug delivery devices that have needle guard mechanisms with interference arrangements, which provide a tunable threshold of resistance to movement of the needle guard that must be overcome by a patient or operator to effect needle insertion.

BACKGROUND

Medications including, but not limited to biologics for the treatment of rheumatoid arthritis, psoriasis, dislypidemia, osteoporosis, and other conditions, may be delivered to the subcutaneous, intramuscular, or intradermal spaces of a patient. Drug delivery devices such as syringes, injectors, and autoinjectors can be used for delivery of such medications by injection.

Injectors and autoinjectors (injectors) are preferred for delivering many types of therapies, in part because they incorporate safety features, which traditional syringes do not provide. For example, it is desirable to provide protection against accidental needle sticks or unintended dosing while handling the injector.

Syringes can be transported with a needle shield in place, which functions as a closure to maintain sterility of the injection needle, and provides a level of protection against accidental needle sticks or unintended dosing while handling the syringe. The needle shield, however, must be removed to allow for drug delivery, thereby exposing the injection needle. As the injection process requires handling of the syringe without the needle shield in place during placement of the needle and delivery of the medication, there exists a safety risk of accidental needle stick or unintended delivery prior to injection.

It is desirable for injectors to protect against risks created by the exposed needle. As shown in FIG. 1, many injectors include a retractable needle guard 52 which surrounds the injection needle 24 to protect against accidental needle sticks or unintended dosing after the needle shield 29 has been removed. The needle guard 52 requires an input force to expose the injection needle 24. This input force represents the user's intent to expose or insert the needle for injection. In the absence of input force, the needle guard 52 remains extended over the needle 24.

The needle guard 24 can protect against unintended dosing by resisting the force tending to expose and/or insert the injection needle until a threshold input force is achieved. Several prior art mechanisms have been developed to provide this resistive force. Many of these mechanisms use springs to provide the resistive force, for example, as shown in FIG. 1 (spring 60). Other devices utilize automatic needle insertion mechanisms to provide resistive force. The use of springs or automatic needle insertion mechanisms, however, adds complexity and additional components to the drug delivery device. The automatic needle insertion mechanisms, in particular, add complexity that can reduce the reliability of the injector and increase cost of the device.

Automatic needle insertion mechanisms provide energy to insert the injection needle. Some of these mechanisms may use one or more springs (hereinafter spring), which provide the potential energy to insert the injection needle. Prior to release, the spring stores potential energy. As the spring is compressed, the potential energy increases, until the release threshold is achieved and the potential energy is converted to kinetic energy, subject to acceleration and/or deceleration. As the active mass of the injector makes contact with the resisting force of the spring, the kinetic energy defines the inertia as a function of the active mass and speed of the active mass of the injection system, which in turn defines the speed and force of needle insertion. Hence, the potential energy of the spring can be adjusted to provide an optimal needle insertion speed and force. One of the benefits of the automatic needle insertion mechanism is the ability to optimize the needle insertion process.

Accordingly, a drug delivery device with improved reliability, lower cost, and optimized needle insertion, is desired.

SUMMARY

A drug delivery device comprising: a casing for housing a drug storage container, the drug storage container including a dose delivery member, at least an insertion portion of the dose delivery member extending through an opening in the casing; a needle guard movable relative to the casing between extended and retracted positions, the insertion portion of the dose delivery member being surrounded by the guard in the extended position and the insertion portion of the dose delivery member being at least partially exposed when the guard is in the retracted position; an interference arrangement for providing selected threshold of resistance to movement of the guard from the extended position to the retracted position during insertion of the dose delivery member into body tissue at an injection site, the detent arrangement having a first member associated with a surface within the casing, and a second member extending from the guard, the first and second members engaging one another to retain the guard in the extended position, one of the first and second members moving if the selected threshold of resistance is exceeded to allow the members to slide past one another to allow the guard to move into the retracted position when the device is pressed toward the injection site during insertion of the dose delivery member.

Further, a method for administering a drug comprising: providing an delivery device comprising a casing, a guard, and an interference arrangement, the casing for housing a drug storage container, the drug storage container including a dose delivery member at least partially extending through an opening in the casing, the guard movable relative to the casing between extended and retracted positions, the dose delivery member concealed by the guard in the extended position and the dose delivery member exposed when the guard is in the retracted position, the interference arrangement having a first member associated with a surface within the casing, and a second member extending from the guard, the first and second members engaging one another to retain the guard in the extended position; and pressing the guard against body tissue at an injection site to insert the dose delivery member into the tissue, the interference arrangement providing a threshold of resistance to movement of the guard from the extended position, one of the first and second members moving if the threshold of resistance is exceeded to allow the members to slide past one another as the guard starts to move toward the casing into the retracted position.

BRIEF DESCRIPTION OF THE DRAWINGS

The same reference numerals are used in the drawings to identify the same or similar elements and structures in the various embodiments.

GENERAL DESCRIPTION

Figure 1:
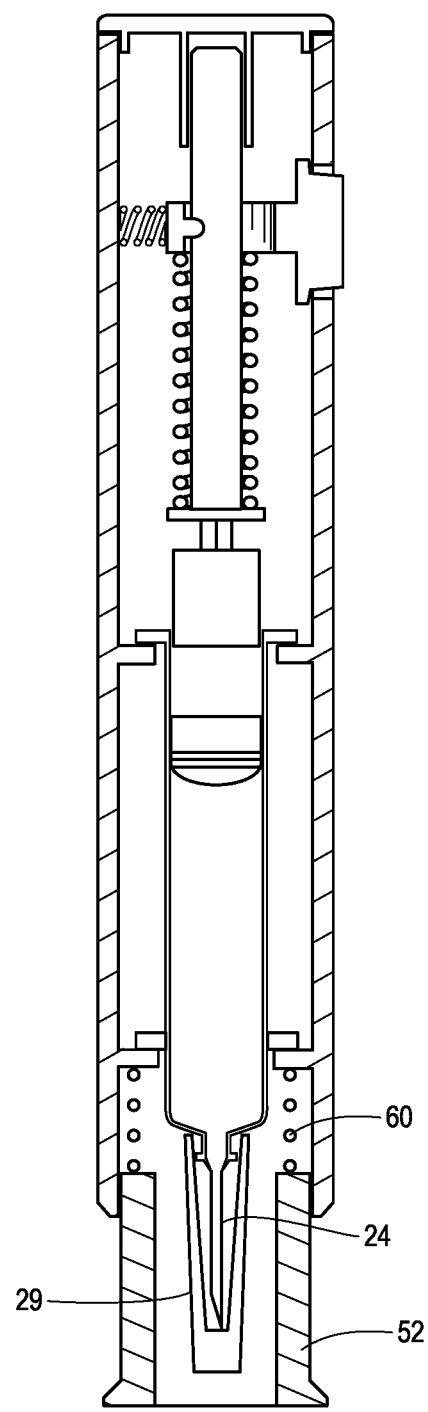
FIG. 1 is an elevational view in partial cross-section of a prior art drug delivery device.

Disclosed herein is a drug delivery device. In various embodiments the device comprises: a casing having an opening, the casing configured to contain a drug storage container including a dose delivery member such that at least an insertion portion of the dose delivery member is configured to extend through the opening in the casing; a needle guard disposed adjacent to the opening and movable relative to the casing between an extended position and a retracted position, the insertion portion of the dose delivery member being surrounded by the needle guard in the extended position and the insertion portion of the dose delivery member being at least partially exposed when the needle guard is in the retracted position; an interference arrangement for providing a selected threshold of resistance to movement of the needle guard from the extended position to the retracted position during insertion of the dose delivery member into body tissue at an injection site, the interference arrangement having a first member associated with a surface of the casing, and a second member extending from the needle guard, the first and second members engaging one another to retain the needle guard in the extended position, one of the first and second members moving if the selected threshold of resistance is exceeded to allow the members to slide past one another and to allow the needle guard to move into the retracted position when the device is pressed toward the injection site during insertion of the dose delivery member.

Further disclosed herein is a method for administering a drug. The method comprises: providing a delivery device comprising a casing, a needle guard, and an interference arrangement, the casing for housing a drug storage container, the drug storage container including a dose delivery member at least partially extending through an opening in the casing, the needle guard movable relative to the casing between extended and retracted positions, the dose delivery member concealed by the needle guard in the extended position and the dose delivery member exposed when the needle guard is in the retracted position, the interference arrangement having a first member associated with a surface within the casing, and a second member extending from the needle guard, the first and second members engaging one another to retain the needle guard in the extended position; and pressing the needle guard against body tissue at an injection site to insert the dose delivery member into the tissue, the interference arrangement providing a threshold of resistance to movement of the needle guard from the extended position, one of the first and second members moving if the threshold of resistance is exceeded to allow the members to slide past one another as the needle guard starts to move toward the casing into the retracted position.

Further still disclosed herein is a drug delivery device comprising: a casing configured to contain a drug storage container with a dose delivery member for delivering a dose of the drug to a patient; a needle guard disposed adjacent to an opening in the casing from which the dose delivery member would extend, the needle guard being movable relative to the casing between an extended position for surrounding the dose delivery member and a retracted position for exposing the dose delivery member; and an interference arrangement providing a selected threshold of resistance that must be overcome in order to move the needle guard from the extended position to the retracted position, the interference arrangement having a first member associated with a surface of the casing, and a second member associated with the needle guard, the first and second members contacting each other when the needle guard is in the extended position, wherein at least one of the first and second members is carried by a flexible arm such that upon application of an axial force urging the needle guard from the extended position toward the retracted position, the flexible arm flexes to move the associated first and/or second member radially away from the other to allow the first and second members to slide past one another.

DETAILED DESCRIPTION

Figure 2A:
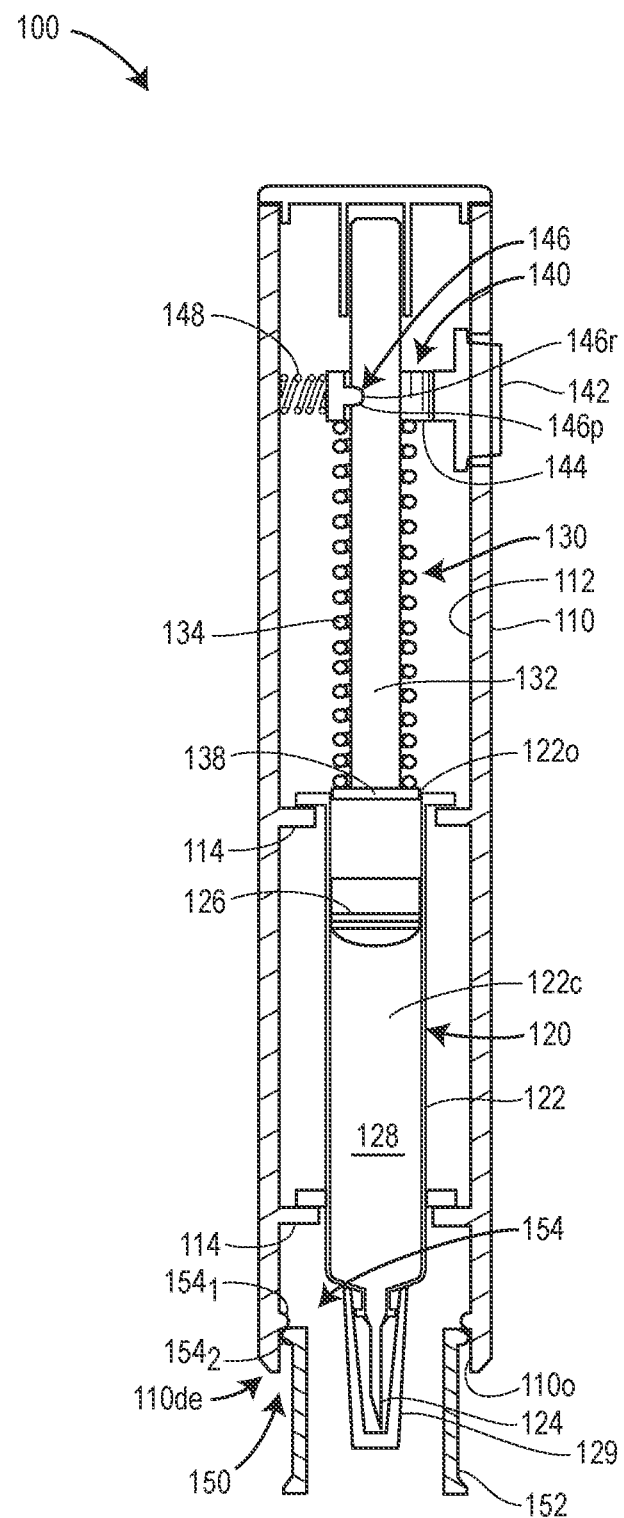
FIG. 2A is an elevational view in partial cross-section of an embodiment of a drug delivery device according to the present disclosure.

FIG. 2A shows an embodiment of a hand-held drug delivery device 100 according to the present disclosure, which comprises a needle guard mechanism 150 having a tunable threshold of resistance to movement of a needle guard 152 to effect and optimize needle insertion, speed and force. The drug delivery device 100 can be configured as a single-use, disposable injector or a multiple-use reusable injector. The drug delivery device 100 can be configured to deliver any suitable medicament or drug including those having a viscosity which can range, for example, from about 1-200 centipoise. Further, the drug delivery device 100 can be configured as an autoinjector for self-administration, although such devices can also be used by a caregiver or a formally trained healthcare provider to administer an injection. Referring to FIG. 2A, the drug delivery device 100 in various embodiments can further comprise an elongated housing or outer casing 110 that holds a drug storage device 120. The drug storage device 120 in various embodiments can include a primary container 122, a stopper 126 moveably disposed in an interior chamber 122c of the primary container 122 for expelling a medicament or drug 128 contained therein, and an injection needle 124 (as shown), cannula or any other suitable dose delivery member or element capable of penetrating body tissue and dispensing a drug into the body of a patient. In some embodiments, the drug storage device 120 may comprise a conventional glass or plastic syringe or cartridge. A removable shield 129 can be installed over the injection needle 124 for maintaining same in a sterile state prior to use of the drug delivery device 100. The drug storage device 120 may be prefilled with the one or more doses of the medicament or drug 128.

In various embodiments, the interior surface 112 of the casing 110 can include one or more support members 114 for holding the drug storage device 120 in a fixed manner within the outer casing 110 with at least an insertion portion of the injection needle 124 extending through an opening 110o defined in a distal end 110de of the casing 110.

Referring still to FIG. 2A, various embodiments of the drug delivery device 100 can further comprise an injection drive mechanism 130 and a drive triggering mechanism 140. The injection drive mechanism 130 can be disposed within the casing 110 and in some embodiments may comprise a plunger 132 and a plunger drive spring 134 for propelling the plunger 132 into and through the primary container 122 of the drug storage device 120 to perform drug injection or dosing. The plunger 132 and the plunger drive spring 134 can be configured so that the plunger 132 extends through the plunger drive spring 134 with one end of the spring 134 engaging a head member 138 of the plunger 132 and the other end of the spring 134 engaging the drive triggering mechanism 140. Prior to activation of the injection drive mechanism 130, in some embodiments the plunger 132 is in a position where the head member of the plunger 132 is disposed adjacent to the opening 122o of the primary container 122 of the drug storage device 120 with the spring 134 compressed between the head member 138 of the plunger 132 and the drive triggering mechanism 140. When the injection drive mechanism 130 is activated by the drive triggering mechanism 140, the plunger drive spring 134 expands to propel the plunger 132 into and through the primary container 122 of the drug storage device 120 to drive the stopper 126 through the primary container 122 to expel the drug 128 through the injection needle 124.

In other embodiments, the injection drive mechanism 130 of the drug delivery device 100 can comprise an electrical/mechanical arrangement (not shown) comprising one or more motors and/or solenoids and a drive train or transmission, or an arrangement that generates or releases a pressurized gas or fluid (not shown), to propel the plunger 132. Such injection drive mechanisms are well known in the art. In further embodiments, the injection drive mechanism 130 may comprise a mechanical arrangement that generates or releases a pressurized gas or fluid (not shown) which acts directly on the stopper 126 to move it through the primary container 122 to expel the drug 128 therefrom through the injection needle 124. Such injection drive mechanisms are well known in the art.

Referring still to FIG. 2A, the drive triggering mechanism 140 can be disposed within the casing 110 and comprise an activation button 142 which extends through an opening in the side of the casing 110, a plunger release arm 144 extending from the activation button 142, and a trigger spring 148 disposed between the plunger release arm 144 and the interior surface 112 of the casing 110. The activation button 142 enables the drive triggering mechanism 140 to be actuated by the patient or other operator, which in turn, activates the injection drive mechanism 130. The plunger release arm 144 is moveable between a plunger hold position and a plunger release position. In some embodiments, in the plunger hold position, the plunger release arm 144 holds the plunger 143 in position via a detent 146. The detent 146 may comprise a projection 146p on the plunger release arm 144 and a recess 146r formed in the side of the plunger 132. In the plunger release position, the plunger release arm 144 disengages the detent projection 146p from the detent recess 146r, which releases the plunger 132 and allows it to be propelled by the plunger drive spring 134. The trigger spring 148 applies a force which maintains the plunger release arm 144 in the plunger hold position with the detent projection 146p and recess 146r engaged. When the activation button 142 is pressed, the force of the trigger spring 148 is overcome and the plunger release arm 144 is moved out of the plunger hold position into the plunger release position, thereby disengaging the detent 146 and releasing the plunger 132.

In other embodiments, the drive triggering mechanism 140 can comprise an electrical/mechanical arrangement (not shown) comprising one or more switches, springs, and/or sensors to activate the injection drive mechanism 130. Such electrical/mechanical arrangements are well known in the art.

Figure 2B:
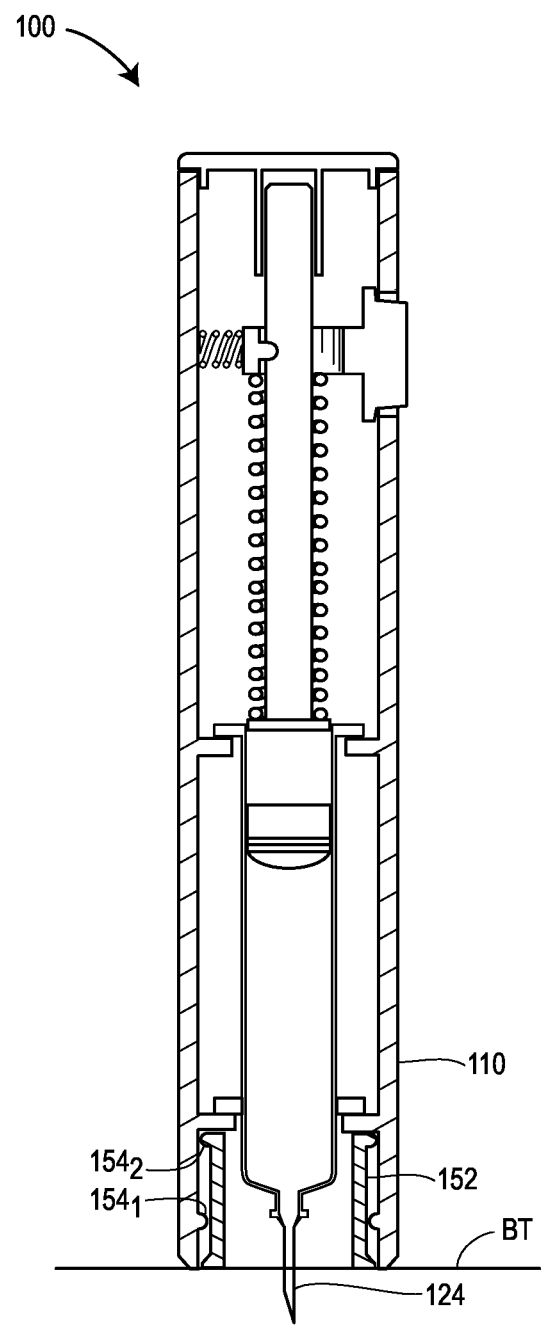
FIG. 2B is an elevational view in partial cross-section of the drug delivery device of FIG. 2B after completion of needle insertion.

Referring still to FIG. 2A, the needle guard mechanism 150 in various embodiments comprises a needle guard 152 movably disposed at the distal end 110de of the casing 110 and a detent or interference arrangement 154. The needle guard 152 could be biased into the position depicted in FIG. 2A with a spring (not shown) similar to spring 60 shown in FIG. 1. The interference arrangement 154 retains the needle guard 152 in an extended position with a tunable or selectable threshold of resistance to the patient's or operator's effort to collapse and release the needle guard 152 and insert the injection needle 124 of the drug storage device 120 into body tissue as shown in FIG. 2B, thereby optimizing needle insertion speed and force and preventing unintended dosing after the needle shield 129 has been removed.

The needle guard 152 in some embodiments can have a tubular structure that surrounds the insertion portion of the injection needle 124 extending from the distal end 110*de* of the casing 110 (extended position) to protect against accidental needle sticks. The needle guard 152 can be configured so that it collapses or retracts into the casing 110, as shown in FIG. 2B, or, in other versions, retracts over the casing 110 (not shown).

The interference arrangement 154 in various embodiments can comprise a first member 1541 associated with the casing 110, and a second member 1542 associated with the needle guard 152. At least portions of the first and second members 1541, 1542 engage one another to retain the needle guard 152 in the extended position and provide the selected threshold of resistance to movement or release of the needle guard 152. In some embodiments, one of the first and second members 1541, 1542 can be configured to move when an axial force is applied to the drug delivery device 100 by the patient or operator pressing the device 100 toward the injection site meets or exceeds the selected threshold of resistance, thereby allowing the other one of the first and second members 1541, 1542 to slide past it to release the needle guard 152 and allow it to retract toward the casing 110 into the retracted position to achieve needle insertion as shown in FIG. 2B.

Figure 3A:
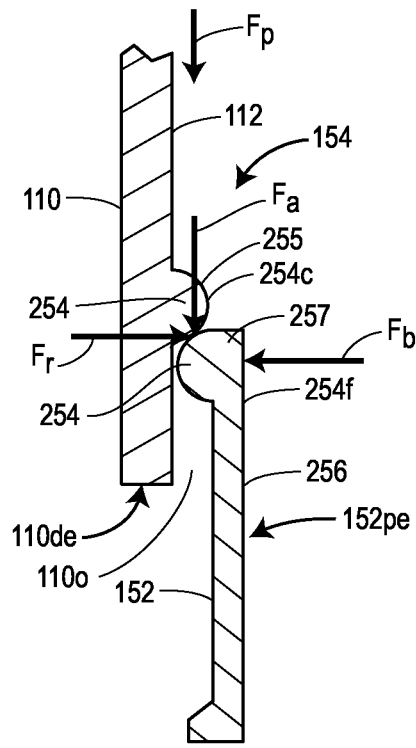
FIG. 3A is an elevational view showing a section of an embodiment of a needle guard mechanism of the drug delivery device and an embodiment of an interference arrangement of the needle guard mechanism.
Figure 3B:
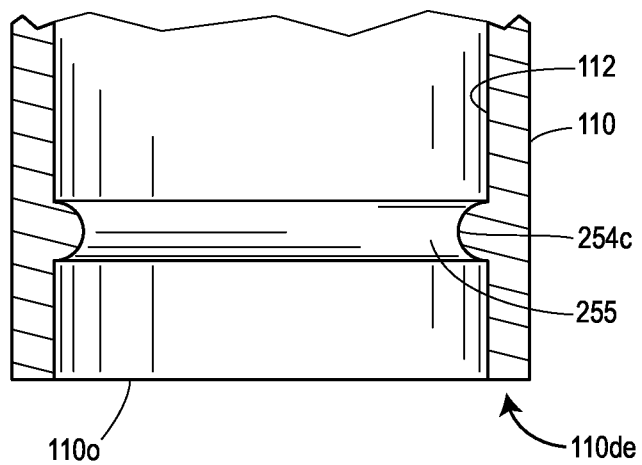
FIG. 3B is a sectional view of the interior of a casing of the drug delivery device showing an embodiment of a cam element of the interference arrangement shown in FIG. 3A.
Figure 3C:
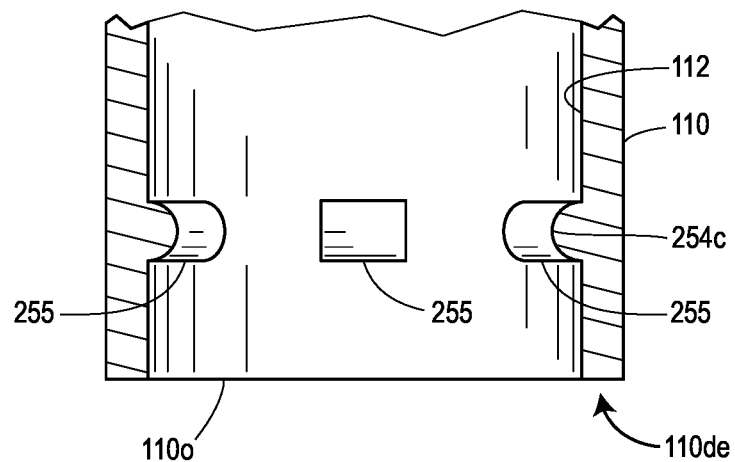
FIG. 3C is a sectional view of the interior of the casing of the drug delivery device showing another embodiment of the cam element of the interference arrangement shown in FIG. 3A.
Figure 3D:
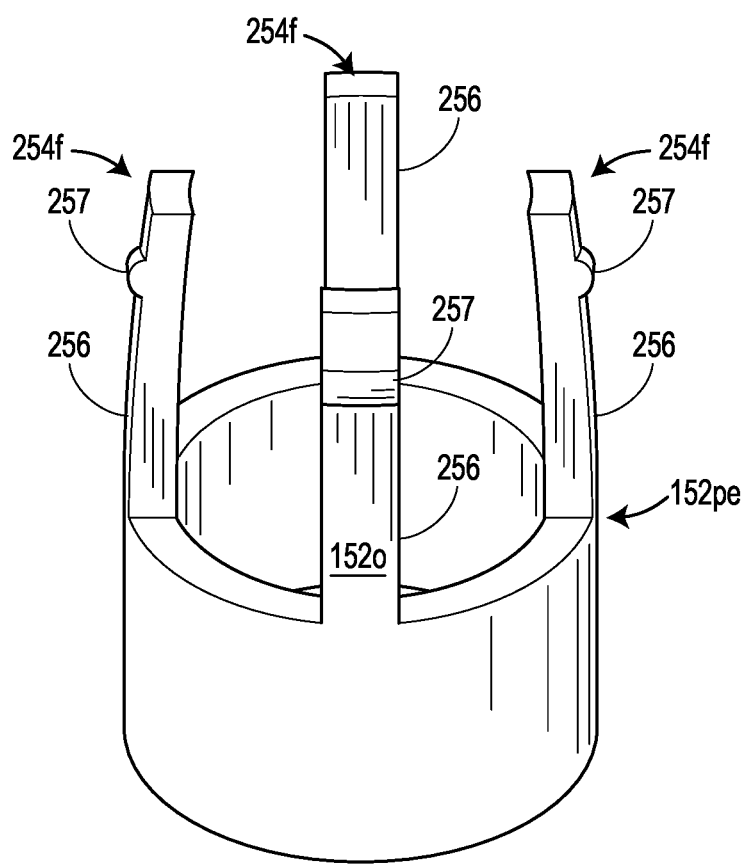
FIG. 3D is a perspective view of a needle guard showing an embodiment of a cam follower of the interference arrangement shown in FIG. 3A.

Referring to FIG. 3A, in some embodiments the interference arrangement 154 can comprise an overcenter cam mechanism 254 comprising a fixed cam element 254*c* and one or more resiliently biased cam followers 254*f*. As shown in FIG. 3B, the fixed cam element 254*c* can comprise a circumferential bead 255 disposed on the interior surface 112 of the casing 110 adjacent to the opening 110*o* at the distal end 110*de* of the casing 110. The circumferential bead 255 can be continuous as shown in FIG. 3B or segmented as shown in FIG. 3C. As shown in FIG. 3D, the one or more of the resiliently biased cam followers 254*f* can comprise a flexible arm 256 that extends from a proximal end 152*pe* of the needle guard 152 and a projection 257 disposed on an outwardly facing surface 152*o* of the flexible arm 256. As shown in FIG. 3A, the one or more flexible arms 256 bias their corresponding projections 257 against the fixed circumferential bead cam element 255 (or elements in segmented embodiments).

As also illustrated in FIG. 3A, the fixed cam element 254*c* on the casing 110 and the cam followers 254*f* on the needle guard 152 include rounded (e.g., cammed or bulbous) external surfaces (e.g., profiles) to facilitate sliding interaction during use of the drug delivery device 100. For example, as a user applies an axial force $F_p$ to the drug delivery device 100, a generally equal and opposite axial force is applied to the needle guard 152 urging the needle guar 152 toward its retracted position. But, the engagement of the cam element 254*c* and cam followers 254*f* prevents substantial retraction until the threshold of resistance is overcome. That is, in the version of FIG. 3A, the threshold of resistance is equal to the force required to cause the flexible arms 256 carrying the cam followers 254*f* to deflect away from the fixed cam element 254 such that the rounded outer surfaces of the cam followers 254*f* are able slide relative to and beyond the fixed cam element 254*c*. In FIG. 3A, the force applied by the user is shown as $F_p$, and this translates into the fixed cam element 254*c* applying an axial force component $F_a$ and a radial force component $F_r$ on each of the cam followers 254*f*. Thus, in order to overcome the threshold of resistance, the axial force $F_p$ applied by the user must be large enough to create a radial force component $F_r$ that is sufficient to overcome a natural resistive bias force Fb of the flexible arms 256. The resistive bias force Fb of the flexible arms 256 is primarily dependent on the material from which the arms 256 are constructed and the geometry of the arms 256 (e.g., the length of the arms 256, the width of the arms 256, the thickness of the arms 256, a cross-sectional shape of the arms, etc.).

Figure 4:
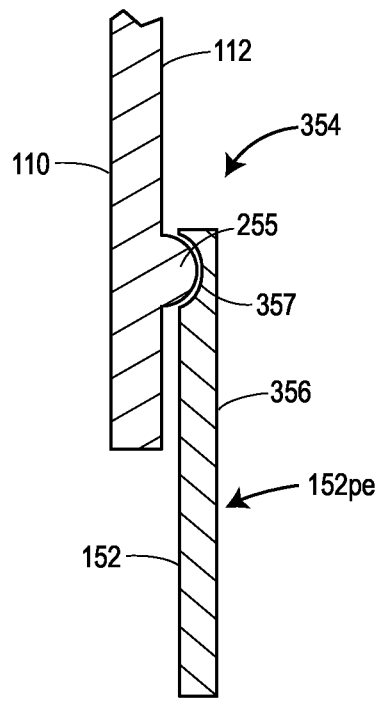
FIG. 4 is an elevational view showing a section of the needle guard mechanism of the drug delivery device showing another embodiment of the interference arrangement.

Referring to FIG. 4, various embodiments of the overcenter cam mechanism 354 can comprise the circumferential bead 255 disposed on the interior surface 112 of the casing 110 as described earlier with respect to FIGS. 3A-3C, and one or more of the resiliently biased cam followers 356*f* configured as a rounded groove 357 formed in the flexible arm 356 that extends from the proximal end of the needle guard 152. The one or more flexible arms 356 bias their corresponding grooves 357 against the circumferential bead 255.

Figure 5:
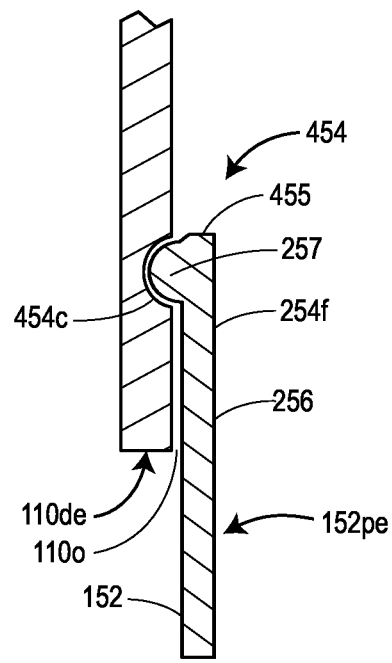
FIG. 5 is an elevational view showing a section of the needle guard mechanism of the drug delivery device showing another embodiment of the interference arrangement.

FIG. 5 shows one embodiment of the overcenter cam mechanism 454 where the cam element 454*c* comprises a continuous or segmented circumferential groove 455 formed in the interior surface 112 of the casing 110 adjacent to the opening 110*o* at the distal end 110*de* of the casing 110. In this embodiment, the one or more flexible arms 256 bias their corresponding projections 257 against the fixed circumferential groove 455.

Figure 6:
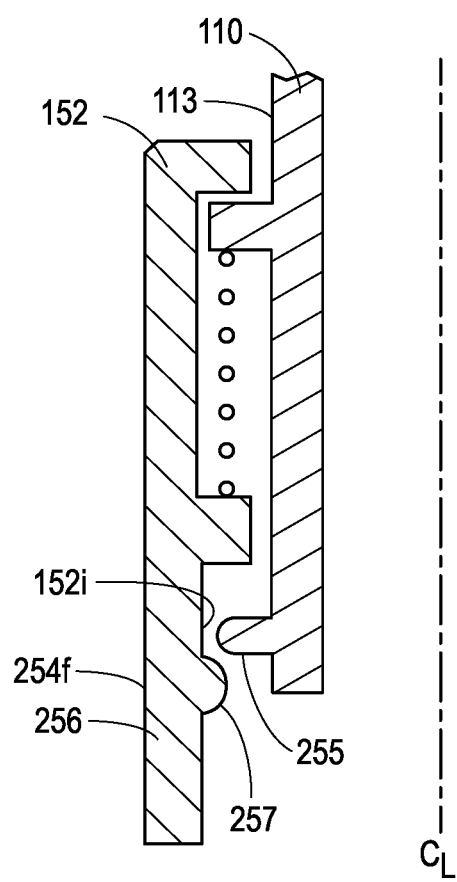
FIG. 6 is an elevational view showing a section of another embodiment of the needle guard mechanism of the drug delivery device and another embodiment of the interference arrangement of the needle guard mechanism.

Referring to FIG. 6, in further embodiments, the needle guard 152 can be configured to retract over the exterior surface 113 of the casing 110. In such embodiments, the fixed continuous or segmented circumferential bead 255 can be provided on the exterior surface 113 of the casing 110 and the projections 257 of the resiliently biased cam followers 254*f* can be provided on the inner surfaces 152*i* of the flexible arms 256.

Figure 7A:
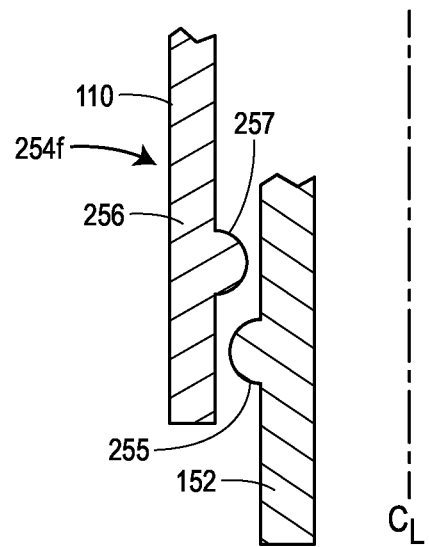
FIGS. 7A and 7B are elevational views of showing sections of another embodiment of the needle guard mechanism and the interference arrangement and the operation thereof.
Figure 7B:
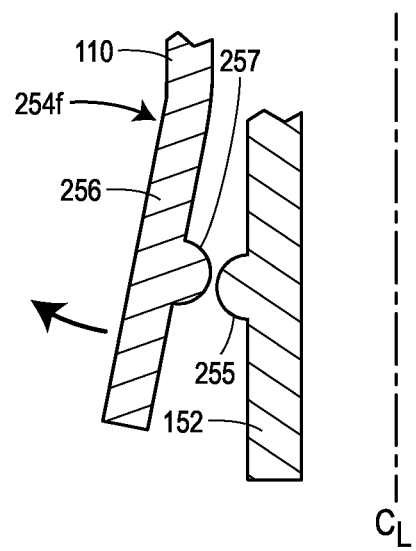

Referring to FIGS. 7A and 7B, in still other embodiments, the needle guard 152 can include the earlier described fixed continuous or segmented circumferential bead 255 on an outer surface thereof and the casing 110 can include the one or more resiliently biased cam followers 254*f* including the flexible arms 256 and the projections 257.

The interference arrangement can be configured to provide desired potential and kinetic energies as well as a desired inertia at the moment of injection needle contact with the body tissue. The force required to overcome the interference arrangement and the driven mass (device and patient/operator) represents the potential energy at the release of the needle guard. This potential energy converts to kinetic energy as the interference arrangement releases the needle guard, subject to acceleration/deceleration. As the injection needle makes contact with the resistance of the body tissue, the kinetic energy defines the speed and force of approach. By optimizing the potential and kinetic energies, the speed and force of needle insertion can be defined at the moment of injection needle contact, therefore, optimizing the patient's experience to a level equal that may be equal to or better than automatic needle insertion mechanisms.

While each of the embodiments described above with reference to FIGS. 2A-7B include one or more resiliently biased cam followers on only one of the needle guard 152 (e.g., FIGS. 2A-6) or the casing 110 (e.g., FIGS. 7A-7B), other versions can include resiliently biased elements on both the needle guard 152 and the casing 110. For example, in one version, the casing 110 could include a number of segmented circumferential beads, each carried by a flexible arm, and the needle guard 152 could include a corresponding number of cam followers, each carried by a flexible arm. Of course, in other versions, the needle guard 152 could include a number of segmented circumferential beads, each carried by a flexible arm, and the casing 110 could include a corresponding number of cam followers, each carried by a flexible arm. In these alternative constructions, the flexible arms on the casing 110 and the flexible arms on the needle guard 152 could deflect simultaneously in response to a force intending to overcome the resistive force of the interference arrangement, and this could provide for greater flexibility in patient-specific tuning of the interference arrangement.

Figure 8:
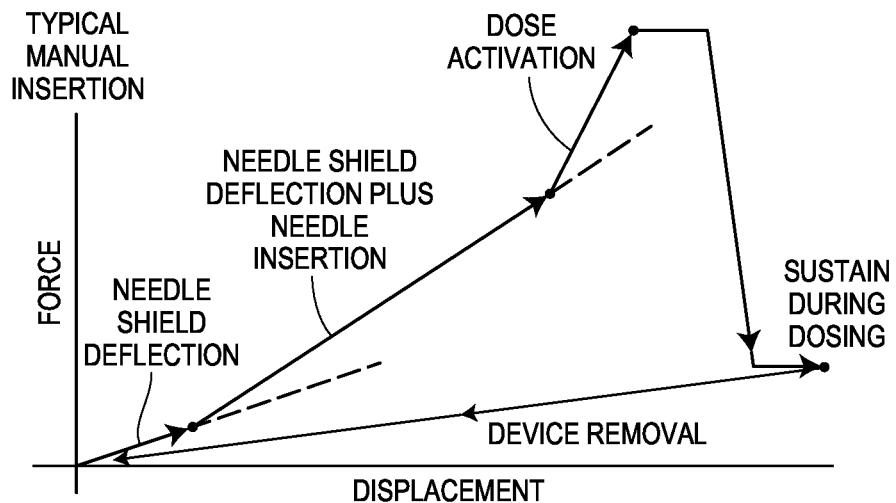
FIG. 8 is a graph plotting effort versus distance for an injector with a conventional manual spring-based needle insertion mechanism.

FIG. 8 is a graph plotting effort versus distance for a prior art injector with a conventional, manual spring-based needle insertion mechanism. Starting from zero time and force, a force can be observed which rises from approximately zero (although the residual force on the needle guard spring can be adjusted to greater than zero to increase the starting force) and ramps up essentially linearly over until the injection needle is presented at the body tissue. In FIG. 8, the force to insert the injection needle overlays the force of the needle guard spring. Thus, during needle insertion, the patient or operator is providing effort to overcome both the force of the needle guard spring and the force to insert the injection needle into the body tissue. As the injection needle approaches full insertion depth, a second mechanism is presented to initiate automatic dosing. As shown in FIG. 8, this second mechanism appears as a sharp rise in effort, which indicates an option to provide further feedback to the patient or operator that dosing will initiate as a result of increased effort, although dosing can continue without this additional feedback to the patient or operator. This rise continues until the threshold force is achieved to activate dosing, at which time the force drops off with delivery.

Figure 9:
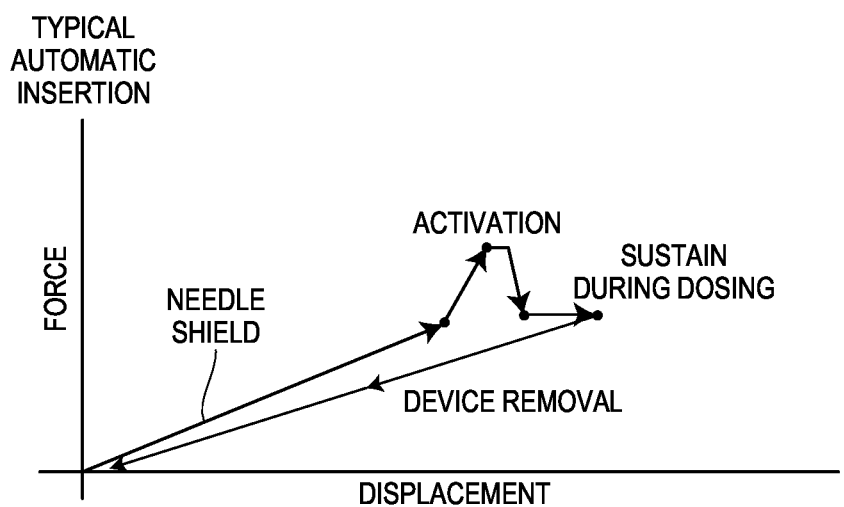
FIG. 9 is a graph plotting effort versus distance for an injector having a conventional automatic needle insertion mechanism.

FIG. 9 is a graph plotting effort versus distance for a prior art injector having a conventional automatic needle insertion mechanism. Starting from zero time and force, a force can be observed which rises from approximately zero (again the starting force can be biased by adjusting the residual force of the resisting spring) and ramps up essentially linearly until the injection needle is presented at the body tissue. In FIG. 9, the force to insert the injection needle is independent of the force of the needle guard spring, however, there is an inertial effect which tends to be perceived as an additional force to be overcome to maintain the injector in intimate contact with the body tissue. As the injection needle approaches full insertion depth, the automatic mechanism continues to apply load to the drug container to force the full dose out through the injection needle. There is residual force to overcome during drug delivery to prevent the needle guard from extending to cover the injection needle. The residual force may also tend to push the injection needle from the body tissue.

Figure 10:
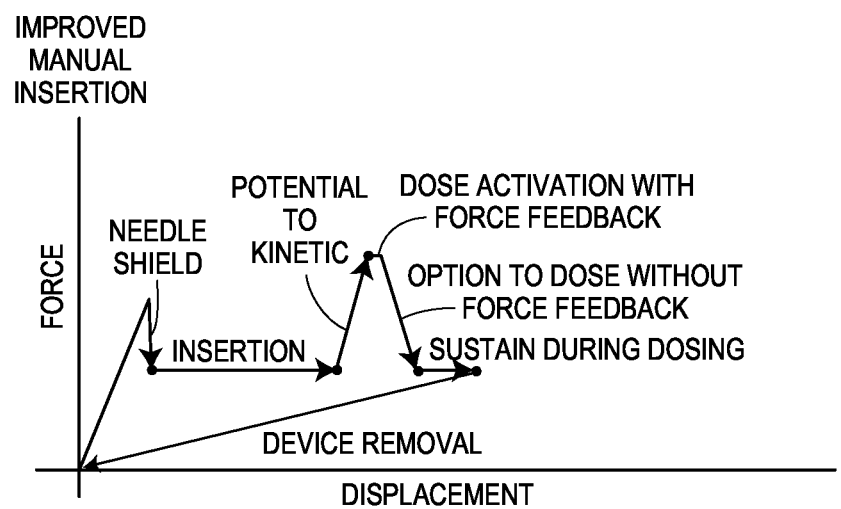
FIG. 10 is a graph plotting effort versus distance for an embodiment of the drug delivery device of the present disclosure having the needle guard with the interference arrangement.

FIG. 10 is a graph plotting effort versus distance for an embodiment of the drug delivery device of the present disclosure having the needle guard with the interference arrangement. Starting from zero time and force, there a relatively rapid rise in the force required as the needle guard is first brought into contact with the body tissue. The rise represents the force to overcome the resistance provided by the interference arrangement. The magnitude of this force can be selectively adjusted via the interference arrangement to tune the inertia available as needle guard release occurs, thus tuning the needle insertion experience to patient preference. Tuning can be achieved by adjusting one or more of the geometric shape, the dimensions, and the modulus of elasticity of the elements of the interference arrangement. Dosing can occur manually (as some patients of certain therapeutics prefer) or automatically. In the case of automatic dosing, the dosing release (i.e., activation of the injection drive) can occur either independently as shown in FIG. 10, or can occur simultaneously to the insertion release so than needle insertion and the start of dosing occur at the same time.

As can be seen in FIGS. 9 and 10, the injector with the conventional automatic needle insertion mechanism has force that builds with deflection of the needle guard and compression of the needle guard spring. The force for guard release occurs over the relatively long distance and therefore, the patient or operator is not provided with a clear indicator that they are near the point of activation. In a preferred embodiment, the force (resistance) for guard release occurs over a short distance so that there is stronger feedback to the patient or operator, which indicates that they are approaching the point of needle insertion. The duration of this activation event can be adjusted via the interference arrangement of the needle guard mechanism to optimize the patient or operator experience.

Although the needle guard mechanism has been disclosed herein with reference to a hand-held drug delivery device, the needle guard mechanism can also be used in on-body drug delivery devices including injectors and autoinjectors, which are worn on the body of the patient.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is the primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17

(N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery device, needle guard mechanism, systems, methods, and elements thereof have been described in terms of exemplary embodiments, they are not limited thereto. Rather, the appended claims should be construed broadly to include other variants and embodiments of same, which may be made by those skilled in the art without departing from the scope and range of equivalents of the device, needle guard mechanism, systems, methods, and their elements.

What is claimed is:

1. A drug delivery device comprising:
   a housing having an opening;
   a drug storage container including a body portion having a proximal end and a distal end and a delivery member positioned at the distal end of the body portion, the delivery member having an insertion end configured to extend at least partially through the opening during drug delivery;
   a plunger moveable in a distal direction with respect to the drug storage container to expel a drug from the drug storage container through the delivery member;
   a drive positioned at least partially within the housing and storing energy for moving the plunger in the distal direction;
   a guard positioned adjacent to the opening and movable relative to the housing between an extended position and a retracted position, the delivery member, prior to operation of the drug delivery device when the guard is in the extended position, extending through the opening in the housing such that at least a first portion of the delivery member is inside of the housing and at least a second portion of the delivery member including the insertion end of the delivery member is outside of the housing;
   a guard biasing member configured to urge the guard in the distal direction, wherein at least a portion of the guard biasing member is distal to the proximal end of the body portion of the drug storage container; and
   an arrangement configured to resist relative movement between the guard and the housing until a threshold of resistance is exceeded by a force applied to the guard in a proximal direction, wherein the arrangement includes a first member and a second member coupled with the guard to move jointly with the guard when the guard moves between the extended position and the retracted position, the first member being disposed entirely within the guard and configured to rotate as a result of the force applied to the guard in the proximal direction, the second member comprising a protrusion protruding at least partially in a radially inward direction with respect to at least a portion of the guard that is distal to the protrusion, wherein the radially inward direction is at least substantially perpendicular to a longitudinal axis of the drug delivery device, and wherein the first member contacts at least the protrusion to resist relative movement between the guard and the housing until the threshold of resistance is exceeded by the force applied to the guard in the proximal direction.

2. The drug delivery device of claim 1, wherein at least one of the first member and the second member is configured to move if the threshold of resistance is exceeded by the force applied to the guard in the proximal direction to allow the first member and the second member to slide against one another and the guard to move into the retracted position.

3. The drug delivery device of claim 2, wherein the first member is configured to rotate when the first member and the second member slide against one another.

4. The drug delivery device of claim 3, wherein the first member is configured to rotate with respect to a portion of the housing when the first member and the second member slide against one another.

5. The drug delivery device of claim 1, wherein one of the first member and the second member comprises a cam and the other one of the first member and the second member comprises a cam follower.

6. The drug delivery device of claim 5, wherein the first member comprises the cam follower and the second member comprises the cam.

7. The drug delivery device of claim 1, wherein the threshold of resistance is a selected threshold of resistance.

8. The drug delivery device of claim 7, wherein the selected threshold of resistance depends on at least one of: a geometric shape of the arrangement, a dimension of the arrangement, and a modulus of elasticity of the arrangement.

9. The drug delivery device of claim 1, wherein the second member is integrally formed with the guard.

10. The drug delivery device of claim 1, wherein the insertion end of the delivery member is surrounded by the guard in the extended position and the insertion end of the delivery member being at least partially exposed when the guard is in the retracted position.

11. The drug delivery device of claim 1, wherein the proximal end of the drug storage container and the distal end of the drug storage container are arranged at respective positions along an axis, and wherein the first member is configured to move at least partially in a direction that is not parallel to the axis as a result of the force applied to the guard in the proximal direction.

12. The drug delivery device of claim 1, wherein the plunger is configured to move along the longitudinal axis of the drug delivery device when moving in the distal direction with respect to the drug storage container to expel the drug from the drug storage container.

13. The drug delivery device of claim 12, wherein at least a portion of the protrusion comprises a surface facing at least partially in the proximal direction and configured to slidably engage the first member.

14. The drug delivery device of claim 1, wherein a radial distance between the first member and the longitudinal axis of the drug delivery device is substantially the same when the guard is in the extended position and when the guard is in the retracted position.

15. A method of delivering a drug to a user, the method comprising:

providing a drug delivery device comprising a housing having an opening, a drug storage container having a delivery member having an insertion end, a plunger moveable in a distal direction with respect to the drug storage container to expel a drug from the drug storage container through the delivery member, a drive positioned at least partially within the housing and storing energy for moving the plunger in the distal direction, a guard coupled with the housing, a guard biasing member positioned at least partially distal to a proximal end of the drug storage container, and an arrangement configured to resist relative movement between the guard and the housing until a threshold of resistance is exceeded by a force applied to the guard in a proximal direction, the arrangement including a first member and a second member coupled with the guard to move jointly with the guard when the guard moves between an extended position and a retracted position, the first member being disposed entirely within the guard, the second member comprising a protrusion protruding at least partially in a radially inward direction with respect to at least a portion of the guard that is distal to the protrusion, wherein the radially inward direction is at least substantially perpendicular to a longitudinal axis of the drug delivery device, the delivery member, prior to operation of the drug delivery device when the guard is in the extended position, extending through the opening in the housing such that at least a first portion of the delivery member is inside of the housing and at least a second portion of the delivery member including the insertion end of the delivery member is outside of the housing;

positioning the guard in contact with a user at an injection site; and applying the force to the guard in the proximal direction sufficient to exceed the threshold of resistance and permit relative movement between the guard and the housing, wherein the first member contacts at least the protrusion and rotates as a result of the force being applied to the guard in the proximal direction.

16. The method of claim 15, wherein at least one of the first member and the second member moves if the threshold of resistance is exceeded by the force applied to the guard in the proximal direction to allow the first member and the second member to slide against one another and the guard to move into the retracted position.

17. The method of claim 16, wherein the first member rotates when the first member and the second member slide against one another.

18. The method of claim 15, wherein one of the first member and the second member comprises a cam and the other one of the first member and the second member comprises a cam follower.

19. The method of claim 18, wherein the first member comprises the cam follower and the second member comprises the cam.

20. The method of claim 15, wherein the proximal end of the drug storage container and a distal end of the drug storage container are arranged at respective positions along an axis, and wherein the first member is configured to move at least partially in a direction that is not parallel to the axis a result of the force applied to the guard in the proximal direction.

21. The method of claim 15, wherein the plunger is configured to move along the longitudinal axis of the drug delivery device when moving in the distal direction with respect to the drug storage container to expel the drug from the drug storage container.

22. The method of claim 21, wherein at least a portion of the protrusion comprises a surface facing at least partially in the proximal direction and configured to slidably engage the first member.

23. The method of claim 15, wherein a radial distance between the first member and the longitudinal axis of the drug delivery device is substantially the same when the guard is in the extended position and when the guard is in the retracted position.

* * * * *